(12) United States Patent
Wales et al.

(10) Patent No.: US 11,560,539 B2
(45) Date of Patent: Jan. 24, 2023

(54) REVERSIBLE LIQUID FILTRATION SYSTEM

(71) Applicant: The Automation Partnership (Cambridge) Limited, Royston (GB)

(72) Inventors: Richard Wales, St Neots (GB); Andrew Tait, Westminster (GB); Matthew Paley, Cambridge (GB)

(73) Assignee: The Automation Partnership (Cambridge) Limited

(*) Notice: Subject to any disclaimer, the term of this patent is extended or adjusted under 35 U.S.C. 154(b) by 414 days.

(21) Appl. No.: 16/318,318

(22) PCT Filed: Jul. 18, 2017

(86) PCT No.: PCT/EP2017/068128
§ 371 (c)(1),
(2) Date: Jan. 16, 2019

(87) PCT Pub. No.: WO2018/015386
PCT Pub. Date: Jan. 25, 2018

(65) Prior Publication Data
US 2019/0241856 A1    Aug. 8, 2019

(30) Foreign Application Priority Data
Jul. 19, 2016 (EP) .................... 16180188

(51) Int. Cl.
*C12M 1/00* (2006.01)
*C12M 1/34* (2006.01)
*C12M 1/36* (2006.01)

(52) U.S. Cl.
CPC ............ *C12M 29/10* (2013.01); *C12M 21/00* (2013.01); *C12M 29/00* (2013.01); *C12M 29/04* (2013.01);
(Continued)

(58) Field of Classification Search
CPC ...... C12M 29/10; C12M 21/00; C12M 29/00; C12M 29/04; C12M 29/12; C12M 29/18; C12M 41/40; C12M 41/48; C12M 47/10
See application file for complete search history.

(56) References Cited

U.S. PATENT DOCUMENTS

| 4,889,812 A | * | 12/1989 | Guinn ............... C12M 29/12 435/286.7 |
| 2005/0095700 A1 | * | 5/2005 | Budzowski ........... C12M 29/18 435/325 |
| 2015/0247114 A1 | * | 9/2015 | Gebauer ................ F04B 53/20 435/243 |

FOREIGN PATENT DOCUMENTS

| CN | 104640973 A | 5/2015 |
| CN | 104711188 A | 6/2015 |

(Continued)

OTHER PUBLICATIONS

International Search Report and Written Opinion for PCT/EP2017/068128, dated Oct. 5, 2017.

*Primary Examiner* — William H. Beisner
*Assistant Examiner* — Danielle B Henkel
(74) *Attorney, Agent, or Firm* — Klarquist Sparkman, LLP

(57) ABSTRACT

A reversible liquid filtration system for cell culture perfusion comprises: a bioreactor vessel (B4), for storing the cell culture (L4); a perfusion pump (P7), comprising a reciprocable element (P71) which is movable in opposing first and second pumping directions (dF, dR); a filter (F4); and first and second bi-directional valves (BV1, BV2), each selectively controllable between open and closed positions. The perfusion pump (P7), the filter (F4), and the first and second bi-directional valves (BV1, BV2), together comprise a fluidic circuit in communication with the bioreactor vessel (B4). The bi-directional valves (BV1, BV2) are controllable (Continued)

to open and close in co-ordination with the reciprocating perfusion pump (P7), in order to enable both a two-way filtering flow around the fluidic circuit and also an alternating filtering flow between the bioreactor vessel (B4) and the perfusion pump (P7).

19 Claims, 11 Drawing Sheets

(52) U.S. Cl.
CPC ............ *C12M 29/12* (2013.01); *C12M 29/18* (2013.01); *C12M 41/40* (2013.01); *C12M 41/48* (2013.01); *C12M 47/10* (2013.01)

(56) References Cited

FOREIGN PATENT DOCUMENTS

| | | |
|---|---|---|
| JP | 2004357575 A | 12/2004 |
| WO | WO2005/042768 | 5/2005 |
| WO | WO2014/051503 | 4/2014 |
| WO | WO 2014/195252 A2 | 12/2014 |
| WO | WO2015/039115 | 3/2015 |

\* cited by examiner

REVERSIBLE LIQUID FILTRATION SYSTEM

CROSS REFERENCE TO RELATED APPLICATIONS

This is the U.S. National Stage of International Application No. PCT/EP2017/068128, filed Jul. 18, 2017, which was published in English under PCT Article 21(2), which in turn claims the benefit of European Patent Application No. 16180188.1, filed Jul. 19, 2016, which is incorporated herein in its entirety.

FIELD OF THE INVENTION

The present invention relates to liquid filtration systems for cell culture perfusion, and in particular to a reversible liquid filtration system for cell culture perfusion.

BACKGROUND

Systems for filtering liquids are well known in the art where they take many different forms with the typical function of separating, concentrating or removing constituent elements of a liquid, mixture or suspension. Such systems are employed in the biotechnology and pharmaceutical industries to extract certain biological products such as proteins produced using cell cultures within a bioreactor.

In traditional fed-batch bioreactor systems, cells are cultured in batches whereby cells are inoculated into a fresh medium and the cells rapidly enter a growth phase during which they consume the medium nutrients and waste products accumulate in the culture in addition to the secreted protein of interest. After a certain period of time, the cells transition into a decay phase as the accumulation of waste products creates an environment not supportive of cell metabolism and protein production. At an optimal time in the cell culture process identified through experimentation and monitoring of the state of the culture the run is terminated and the protein is separated from the cell culture as a batch. A number of issues exist with such approaches including the variation in the cell environment over the time of the culture resulting in variation in the quality and fine structure of the protein product.

Perfusion bioreactors are a known alternative system in which the cells are kept in culture whilst replenishing the culture media, thereby allowing the maintenance of a high cell concentration and culture environment over periods of 60 days or more. The achievement of higher cell densities through the constant replenishment of nutrients and depletion of waste products allows much higher cell densities to be achieved and as such higher levels of production of target proteins per unit volume of culture. In order to maintain stable cell culture conditions, retention of the cells within the culture whilst allowing a constant flow of fresh media in and spend culture media out is required. One method of such retention is by filtration of the media allowing the extraction of filtered spent cell culture media.

Typical filtration systems employed in perfusion bioreactors utilise a pump which moves cell culture liquid from a bioreactor through a filter wherein the filtrate (often called "permeate") including waste or target products, is removed from the system and the retentate, including live cells, is returned to the bioreactor. Culture media nutrients may then be replenished by a separate system to maintain the cell culture in a steady, equilibrium state. Such prior art devices employ tangential flow filtration, wherein the majority of the feed flow travels tangentially across the surface of the filter. This provides a reasonably gentle filtration method such that the forces acting on the delicate animal cells are relatively small. Furthermore the tangential flow of liquid across the filter ensures that deposits in the filter, which might cause a blockage, are washed away during the filtration process, increasing the length of time over which the filtration system may be continually run.

Some such systems, often termed "tangential flow filtration" or TFF systems, may be arranged such that flow of the liquid is in one direction around a loop, circulating from the bioreactor through the filter and returning to the bioreactor. TFF systems typically use a peristaltic pump, a multi-chamber diaphragm type pump, or a pump with an impeller, driven magnetically where a single use cell contact part is required. Additionally, it is known to be advantageous to reconfigure the components of a TFF system (including turning the peristaltic pump around) to reverse the flow over a longer period in order to extend the life of the filter.

In other systems, often termed "alternating tangential flow filtration" or ATF systems, only a single connection between the bioreactor and filter is used, with the direction of flow alternating such that liquid travels from the bioreactor to the filter and returns to the bioreactor along the same line. The alternating flow in ATF systems is typically achieved using a reciprocable-type pump, for example a diaphragm pump, which can advantageously be made quite compact. This single connection arrangement has the benefit that the reversal of the liquid flow along the filter helps to dislodge deposits from the filter and thereby prevent blockage.

There are arguments for and against both the TFF and ATF methods and commercial systems are available for both approaches at manufacturing scales considered for manufacturing perfusion based production.

There is no small-scale model for either approach at the scale of current state-of the art cell culture process development scales, but there is a need for such a system. Additionally there is a need for the capability to be able to easily compare the performance of specific production cell lines in development within each of the two alternative technical approaches. Currently the scale of technology makes such routine comparison for cell lines in development too costly in labour and resources to be viable. It would be desirable to provide a filtration system that would address these needs.

SUMMARY OF THE INVENTION

According to an aspect of the invention, there is provided a reversible liquid filtration system for cell culture perfusion, comprising: a bioreactor vessel, for storing the cell culture; a perfusion pump, comprising a reciprocable element which is movable in opposing first and second pumping directions; a filter, comprising a membrane which includes a retentate side and an opposing, permeate side; and first and second bi-directional valves, each selectively controllable between open and closed positions, the perfusion pump, the filter, and the first and second bi-directional valves, together comprising a fluidic circuit in communication with the bioreactor vessel, the system being operable in a circuit flow mode, wherein: the first bi-directional valve is controllable to be open and the second bi-directional valve is controllable to be closed, and the reciprocable element of the perfusion pump is movable in the first pumping direction, in order to displace the cell culture from the bioreactor vessel to the perfusion pump; and the first bi-directional valve is controllable to be closed and the second bi-directional valve is controllable to be open, and the reciprocable element of the perfusion pump is movable in the second pumping direction, in order to displace the cell culture from the perfusion pump back to the bioreactor vessel, so as to displace the cell culture along the retentate side of the filter in a first circuit flow direction around the fluidic circuit, and the first bi-directional valve is controllable to be closed and the second bi-directional valve is controllable to be open, and the reciprocable element of the perfusion pump is movable in the first pumping direction, in order to displace the cell culture from the bioreactor vessel to the perfusion pump; and the first bi-directional valve is controllable to be open and the second bi-directional valve is controllable to be closed, and the reciprocable element of the perfusion pump is movable in the second pumping direction, in order to displace the cell culture from the perfusion pump back to the bioreactor vessel, so as to displace the cell culture along the retentate side of the filter in a second circuit flow direction around the fluidic circuit, the second circuit flow direction being opposite to the first circuit flow direction, and the system being operable in an alternating flow mode, wherein: the first bi-directional valve is controllable to be open and the second bi-directional valve is controllable to be closed; the reciprocable element of the perfusion pump is movable in the first pumping direction, in order to displace the cell culture from the bioreactor vessel along the retentate side of the filter to the perfusion pump in a first alternating flow direction; and the reciprocable element of the perfusion pump is movable in the second pumping direction, in order to displace the cell culture from the perfusion pump along the retentate side of the filter back to the bioreactor vessel in a second alternating flow direction, the second alternating flow direction being opposite to the first alternating flow direction, in each of the circuit flow mode and the alternating flow mode the said displacement of the cell culture through the filter causing a driving fluid pressure on the retentate side of the filter membrane such that permeate material may pass through the membrane from the retentate side to the permeate side.

The provision of bi-directional valves means that the claimed system may be operated in a TFF perfusion mode, wherein the direction of a loop flow may be easily and conveniently reversed. This can advantageously prolong filter life.

Importantly, the bi-directional valves are operable to open and close in co-ordination with the motion of a reciprocating perfusion pump, which is a type of pump conventionally used in ATF, but not TFF, cell perfusion. Since reciprocable-type pumps can be made quite compact, the combination and co-ordination of such a pump with bi-directional valves in a system beneficially allows for a small-scale system which can perform TFF perfusion.

Also importantly, one of the bi-directional valves can be controlled to remain open and the other one to remain closed, in order to enable an alternating flow through the filter (between the bioreactor vessel and the reciprocating perfusion pump) in the manner of a conventional ATF system. The claimed system therefore also provides for ATF perfusion, including the benefit that flow reversal along the filter dislodges particles from the filter and so prevents blockage.

Thus the invention provides one, single system which is configured for both TFF and ATF perfusion, using different control regimes. Accordingly, the claimed system is highly flexible and offers the advantages of both TFF and ATF perfusion.

The reversible liquid filtration system may comprise a controller for controlling the first and second bi-directional valves in co-ordination with the movement of the reciprocable element of the perfusion pump.

The reversible liquid filtration system may further comprise: pressure sensors, configured to detect fluidic pressure at the respective retentate and permeate sides of the filter membrane; and a permeate pump, arranged in fluidic communication with the filter and controllable to apply, based on the detected fluidic pressures, a counter fluid pressure on the permeate side of the filter membrane, in opposition to a residue of the said driving fluid pressure on the retentate side, such that no permeate material may pass through the membrane from the retentate side to the permeate side.

The permeate pump may be controllable to apply the counter fluid pressure, to the permeate side of the filter membrane, at a magnitude which is: equal to the residue of the driving fluid pressure on the retentate side, so as to prevent permeate material from passing through the membrane from the retentate side to the permeate side; or greater than the residue of the driving fluid pressure on the retentate side, so as to reverse the flow through the membrane to partially or fully clear the retentate side of the membrane of permeate material.

Thus, advantageously the filter can be kept clear by a synchronised operation of the permeate pump and the perfusion pump.

The permeate pump may be controllable to control a pressure gradient, between the retentate and permeate sides of the filter membrane, in order to control the passage of permeate material through the membrane, from the retentate side to the permeate side, under the residue of the driving fluid pressure on the retentate side.

The reversible liquid filtration system may comprise a controller for controlling in co-ordination the first and second bi-directional valves, the movement of the reciprocable element of the perfusion pump, and the permeate pump. The reciprocable element of the perfusion pump may comprise a piston.

Alternatively, the reciprocable element of the perfusion pump may comprise a diaphragm.

The bioreactor vessel may comprise at least two separate liquid inlets/outlets.

According to another aspect of the invention, there is provided a reversible liquid filtration system for cell culture perfusion, comprising: a bioreactor vessel, for storing the cell culture; a perfusion pump, comprising a reciprocable element which is movable in opposing first and second pumping directions; a filter, comprising a membrane which includes a retentate side and an opposing, permeate side; and first and second bi-directional valves, each selectively controllable between open and closed positions, the perfusion pump, the filter, and the first and second bi-directional valves, together comprising a fluidic circuit in communication with the bioreactor vessel, wherein, in dependence on the selected positions of the first and second bi-directional valves and the pumping direction, the system is selectively operable between: a reversible circuit flow mode, wherein the cell culture will flow, around the fluidic circuit, in a first circuit flow direction or in a second circuit flow direction which is opposite to the first circuit flow direction; and an alternating flow mode, wherein the cell culture will alternately flow, around only a portion of the fluidic circuit, between a first alternating flow direction and in a second alternating flow direction which is opposite to the first alternating flow direction, and wherein, in each of the circuit flow mode and the alternating flow mode, the perfusion pump is operable to displace the cell culture along the retentate side of the filter to cause a driving fluid pressure on the retentate side of the filter membrane such that permeate material may pass through the membrane from the retentate side to the permeate side.

In the reversible circuit flow mode: the first bi-directional valve may be controllable to be open and the second bi-directional valve may be controllable to be closed, and the reciprocable element of the perfusion pump may be movable in the first pumping direction, in order to displace the cell culture from the bioreactor vessel to the perfusion pump; and the first bi-directional valve may be controllable to be closed and the second bi-directional valve may be controllable to be open, and the reciprocable element of the perfusion pump may be movable in the second pumping direction, in order to displace the cell culture from the perfusion pump back to the bioreactor vessel, so as to displace the cell culture along the retentate side of the filter in the first circuit flow direction around the fluidic circuit, and the first bi-directional valve may be controllable to be closed and the second bi-directional valve may be controllable to be open, and the reciprocable element of the perfusion pump may be movable in the first pumping direction, in order to displace the cell culture from the bioreactor vessel to the perfusion pump; and the first bi-directional valve may be controllable to be open and the second bi-directional valve may be controllable to be closed, and the reciprocable element of the perfusion pump may be movable in the second pumping direction, in order to displace the cell culture from the perfusion pump back to the bioreactor vessel, so as to displace the cell culture along the retentate side of the filter in the second circuit flow direction around the fluidic circuit, and in the alternating flow mode the first bi-directional valve may be controllable to be open and the second bi-directional valve may be controllable to be closed; the reciprocable element of the perfusion pump may be movable in the first pumping direction, in order to displace the cell culture from the bioreactor vessel along the retentate side of the filter to the perfusion pump in the first alternating flow direction; and the reciprocable element of the perfusion pump may be movable in the second pumping direction, in order to displace the cell culture from the perfusion pump along the retentate side of the filter back to the bioreactor vessel in the second alternating flow direction.

The reversible liquid filtration system may comprise a controller for controlling the first and second bi-directional valves in co-ordination with the movement of the reciprocable element of the perfusion pump.

The reversible liquid filtration system may comprise: pressure sensors, configured to detect fluidic pressure at the respective retentate and permeate sides of the filter membrane; and a permeate pump, arranged in fluidic communication with the filter and controllable to apply, based on the detected fluidic pressures, a counter fluid pressure on the permeate side of the filter membrane, in opposition to a residue of the said driving fluid pressure on the retentate side, such that no permeate material may pass through the membrane from the retentate side to the permeate side.

The permeate pump may be controllable to apply the counter fluid pressure, to the permeate side of the filter membrane, at a magnitude which is: equal to the residue of the driving fluid pressure on the retentate side, so as to prevent permeate material from passing through the membrane from the retentate side to the permeate side; or greater than the residue of the driving fluid pressure on the retentate side, so as to reverse the flow through the membrane to partially or fully clear the retentate side of the membrane of permeate material.

The permeate pump may be controllable to control a pressure gradient, between the retentate and permeate sides of the filter membrane, in order to control the passage of permeate material through the membrane, from the retentate side to the permeate side, under the residue of the driving fluid pressure on the retentate side.

The reversible liquid filtration system may comprise a controller for controlling in co-ordination the first and second bi-directional valves, the movement of the reciprocable element of the perfusion pump, and the permeate pump.

The reciprocable element of the perfusion pump may comprise a piston. Alternatively, the reciprocable element of the perfusion pump may comprise a diaphragm.

The bioreactor vessel may comprise at least two separate liquid inlets/outlets.

BRIEF DESCRIPTION OF THE DRAWINGS

Embodiments will now be described, by way of example, with reference to the accompanying figures in which.

DETAILED DESCRIPTION OF EMBODIMENTS OF THE INVENTION

Figure 1:
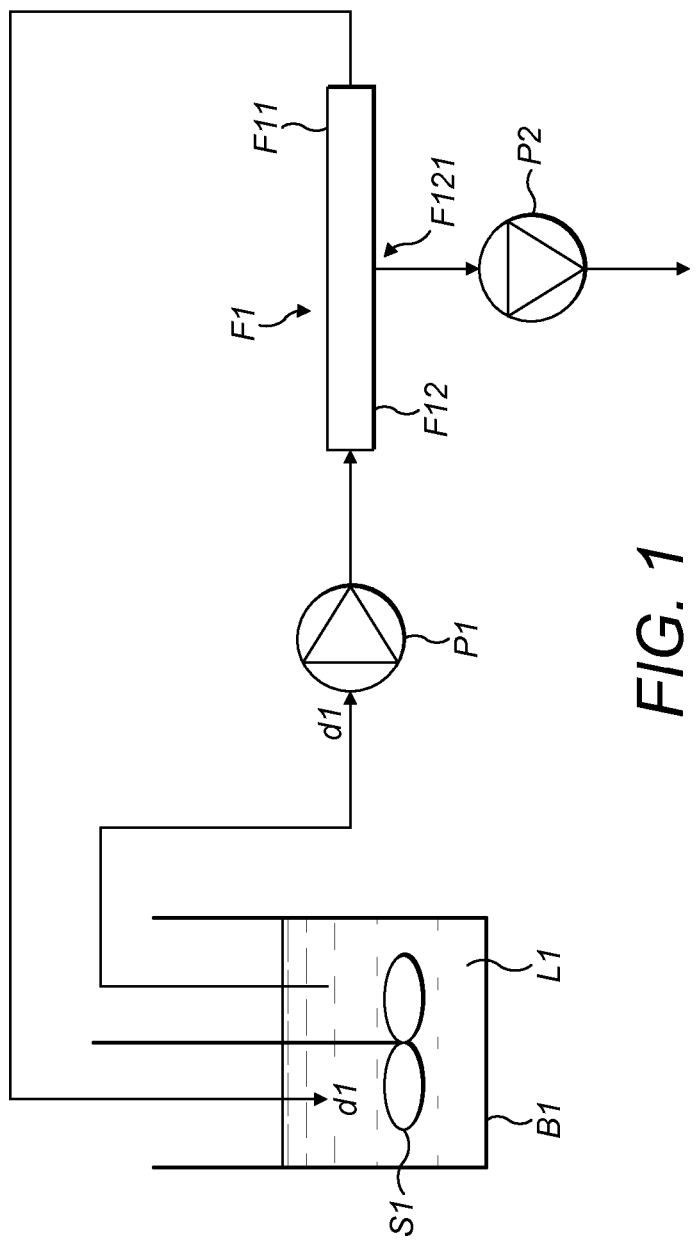
FIGS. 1 to 3b are simplified schematic representations of known filtration systems and operations thereof.

Referring to FIG. 1, a known TFF (tangential flow filtration) system, which is described by US2011/0111486A1, comprises: a bioreactor vessel B1 containing a liquid cell culture L1; a peristaltic-type perfusion pump P1 which is fluidly connected to the bioreactor vessel B1; a filter F1 which comprises a retentate side F11 and a permeate side F12 and which is fluidly connected to the perfusion pump P1 and to the bioreactor vessel B1; and a permeate pump P2 which is fluidly connected to a permeate side outlet F121 of the filter F1. The fluid connections are by means of pipes, hoses, or the like. A stirrer S1 is provided in the bioreactor vessel B1 for agitation of the liquid cell culture L1.

In use, the perfusion pump P1 continuously displaces the cell culture L1 from the bioreactor vessel B1, through the filter F1, and back to the bioreactor vessel B1. Thus the cell culture L1 is filtered and circulates in a "retentate loop" which has one direction d1 only, i.e. anticlockwise in the sense of FIG. 1. The filtered material, or permeate, is moved across the filter F1 due to an increase in trans-membrane pressure, from the retentate side F41 to the permeate side F42, resulting from positive pressure created on the retentate side F41 through the displacement of cell culture L1 from the bioreactor vessel B1 into the filter F1 by the perfusion pump P1, and (optionally) also by a negative pressure created on the permeate side outlet F121 of the filter F1 under the action of the permeate pump P2.

Figure 2A:
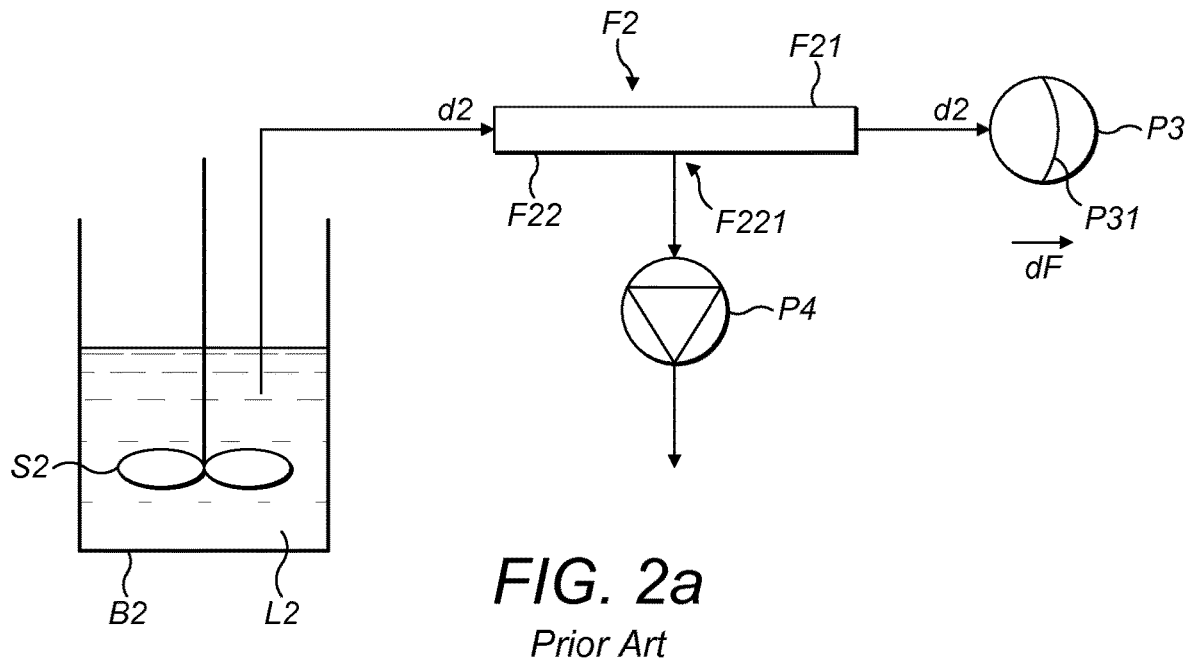
Figure 2B:
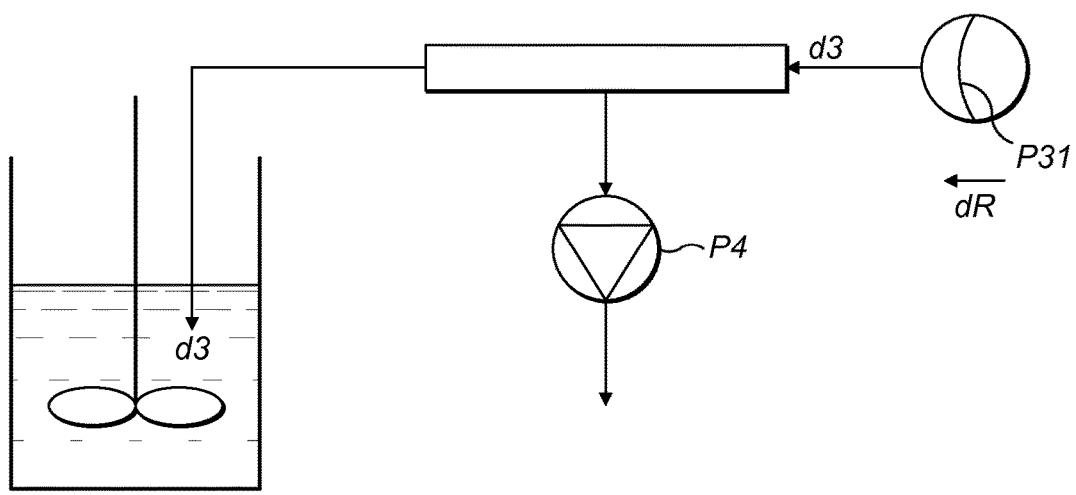

Referring to FIGS. 2a and 2b, a known ATF (alternating tangential flow filtration) system comprises: a bioreactor vessel B2 containing a liquid cell culture L2; a filter F2 which comprises a retentate side F21 and a permeate side F22 and which is fluidly connected to the bioreactor vessel B2; a reciprocable-type perfusion pump P3 which includes a reciprocable element comprising a diaphragm P31 and which is fluidly connected to the filter F2; and a permeate pump P4 which is fluidly connected to a permeate side outlet F221 of the filter F2. The fluid connections are by means of pipes, hoses, or the like. A stirrer S2 is provided in the bioreactor vessel B2 for agitation of the liquid cell culture L2.

Referring in particular to FIG. 2a, in use the diaphragm P31 moves in a forward direction dF (rightwards in the sense of FIG. 2a) to cause displacement of the cell culture L2, in a first flow direction d2, from the bioreactor vessel B2 to the perfusion pump P3 via the filter F2. Referring now to FIG. 2b, after a brief pause, which occurs when the diaphragm P31 has reached the limit of travel in the forward direction dF, the diaphragm P31 moves in a rearward direction dR (leftwards in the sense of FIG. 2b) in order to reversibly displace the filtered cell culture L2 in a second, opposite flow direction d3, back through the filter F2 to the bioreactor vessel B2. The movements are repeated such that the diaphragm P31 continuously reciprocates in the forward and rearward directions dF, dR in order to cycle the cell culture L2 through the filter F2. Thus the cell culture L2 is filtered and the cell culture retentate moves back and forth through the system in two flow directions d2, d3. The filtered material, or permeate, is driven through the filter F2, by a positive pressure created on the retentate side F21 on transfer of the cell culture L2 into the filter F2 on the retentate side F21, either from the bioreactor vessel B2 or from the perfusion pump P3, and additionally through negative pressure on the permeate side F22, created by the action of the permeate pump P4 as the cell culture L2 is drawn out of the permeate side outlet F221 of the filter F2 under the action of the permeate pump P4.

Figure 3A:
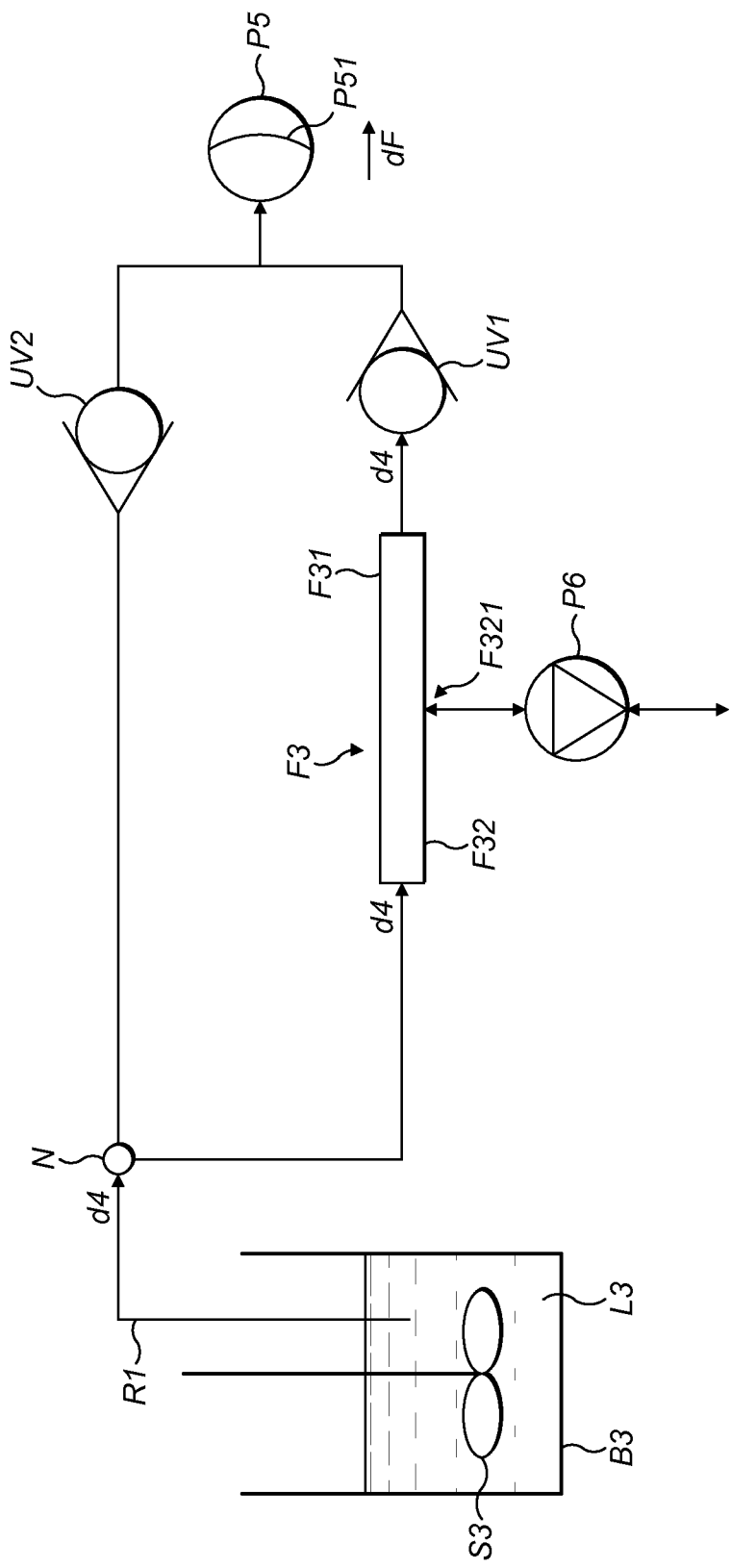
Figure 3B:
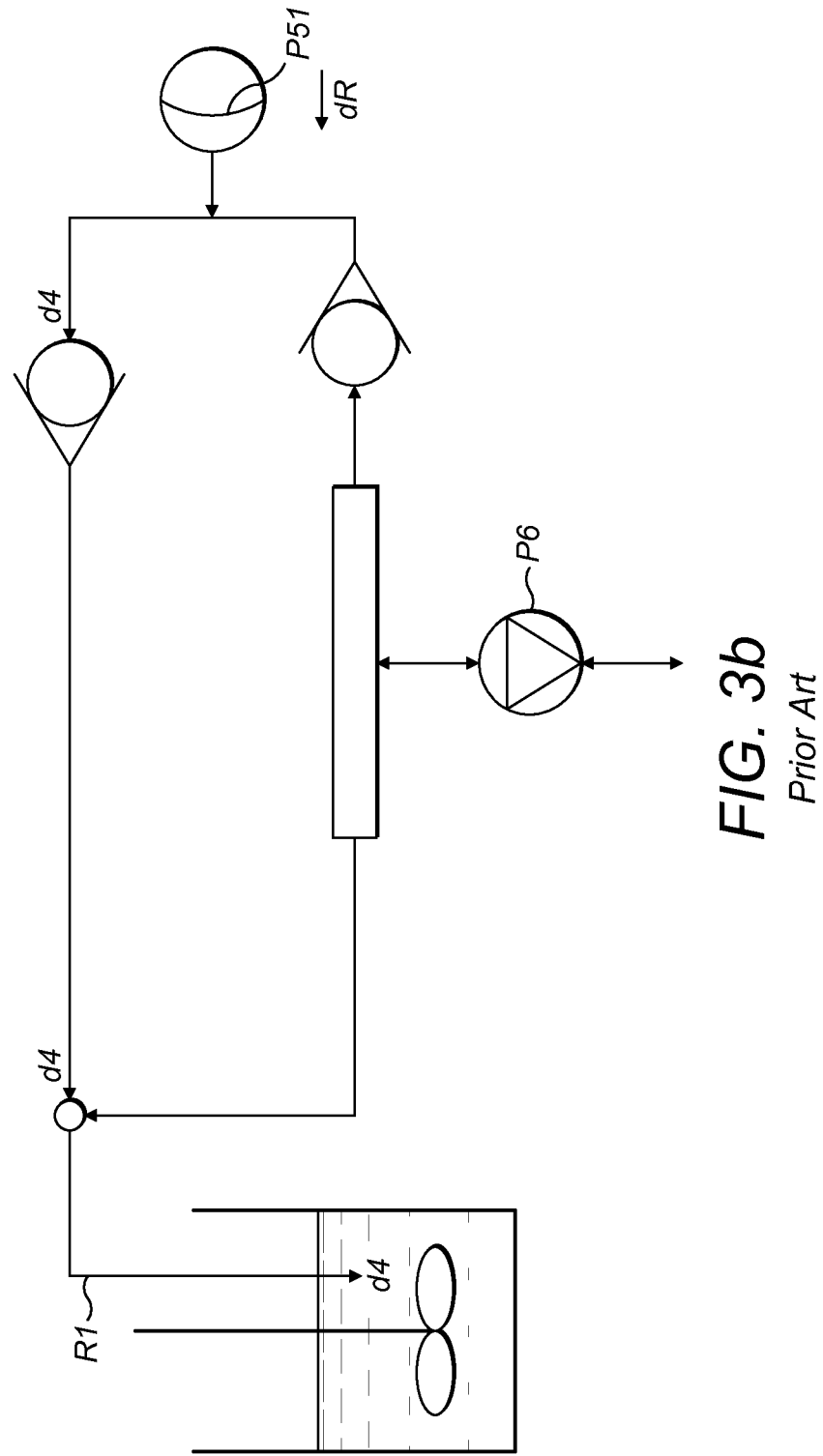

Referring now to FIGS. 3a and 3b, another known TFF system, which is described by WO2014/051503A1, comprises: a bioreactor vessel B3 containing a liquid cell culture L3; a filter F3 which comprises a retentate side F31 and a permeate side F32 and which is fluidly connected to the bioreactor vessel B3 via a branching point or node N; a first one-way or unidirectional valve UV1 which is fluidly connected to the filter F3; a reciprocable-type perfusion pump P5 which includes a reciprocable element comprising a diaphragm P51 and which is fluidly connected to the first unidirectional valve UV1; a second one-way or unidirectional valve UV2 which is fluidly connected to the perfusion pump P5 and to the bioreactor vessel B3 via the node N; and a permeate pump P6 which is fluidly connected to a permeate side outlet F321 of the filter F3. The fluid connections are by means of pipes, hoses, or the like, one of which is arranged so as to provide a single inlet/outlet route R1 at the bioreactor vessel B3 and to branch at the node N which is located distally from the bioreactor vessel B3. A stirrer S3 is provided in the bioreactor vessel B3 for agitation of the liquid cell culture L3.

Referring in particular to FIG. 3a, in use the diaphragm P51 moves in a forward direction dF (rightwards in the sense of FIG. 3a) to cause displacement of the cell culture L3, in a flow direction d4, from the bioreactor vessel B3 to the perfusion pump P5 via the node N, the filter F3 and the first unidirectional valve UV1. Referring now to FIG. 3b, after a brief pause, which occurs when the diaphragm P51 has reached the limit of travel in the forward direction dF, the diaphragm P51 moves in a rearward direction dR (leftwards in the sense of FIG. 3b) in order to displace the filtered cell culture L3, in the flow direction d4, back to the bioreactor vessel B3 via the second unidirectional valve UV2 and the node N. The movements are repeated such that the diaphragm P51 continuously reciprocates in the forward and rearward directions dF, dR in order to cycle the cell culture L3 through the filter F3. Thus the cell culture L3 is filtered and circulates in a "retentate loop" which has one flow direction d4 only, i.e. anticlockwise in the sense of FIGS. 3a and 3b. The unidirectional valves UV1, UV2 serve to allow flow in that direction but to prevent flow in the opposite direction. The filtered material or permeate is drawn out of the permeate side outlet F321 of the filter F3 under the action of the permeate pump P6. The permeate pump P6 may apply a backpressure to the filter F3 in order to flush the filter F3.

Turning to FIGS. 4a to 4d, there is provided a liquid filtration system for cell culture perfusion in accordance with a first embodiment of the invention. In the system a bioreactor vessel B4 contains a liquid cell culture L4. A filter F4 is fluidly connected to the bioreactor vessel B4. The filter F4 comprises a membrane including a retentate side F41 and a permeate side F42. The filter F4 is a tangential flow filter configured so that the flow of liquid cell culture L4 will be substantially tangential to the surface of the retentate side F41. The filter F4 may be a hollow fibre filter.

A first two-way or bi-directional valve BV1 is fluidly connected to the filter F4. A reciprocable-type perfusion pump P7 is fluidly connected to the first bi-directional valve BV1 and includes a reciprocable element. In this embodiment the reciprocable element comprises a diaphragm P71, but may alternatively comprise a piston or some other suitable member arranged for reciprocation. The size of the diaphragm P71 and the extent of its deflection defines a volume of the cell culture L4 to be displaced, as described below. A second two-way or bi-directional valve BV2 is fluidly connected to the perfusion pump P7 and the bioreactor vessel B4. The fluid connections are by means of pipes, hoses, or the like, which, in this exemplary embodiment at least, are arranged so as to include separate and distinct inlet/outlet routes R2, R3 to/from the bioreactor vessel B4. A stirrer (not shown in FIGS. 4a to 4d) may be provided in the bioreactor vessel B4 for agitation of the liquid cell culture L4.

A first TFF (tangential flow filtration) operation of the first embodiment will now be described.

Figure 4A:
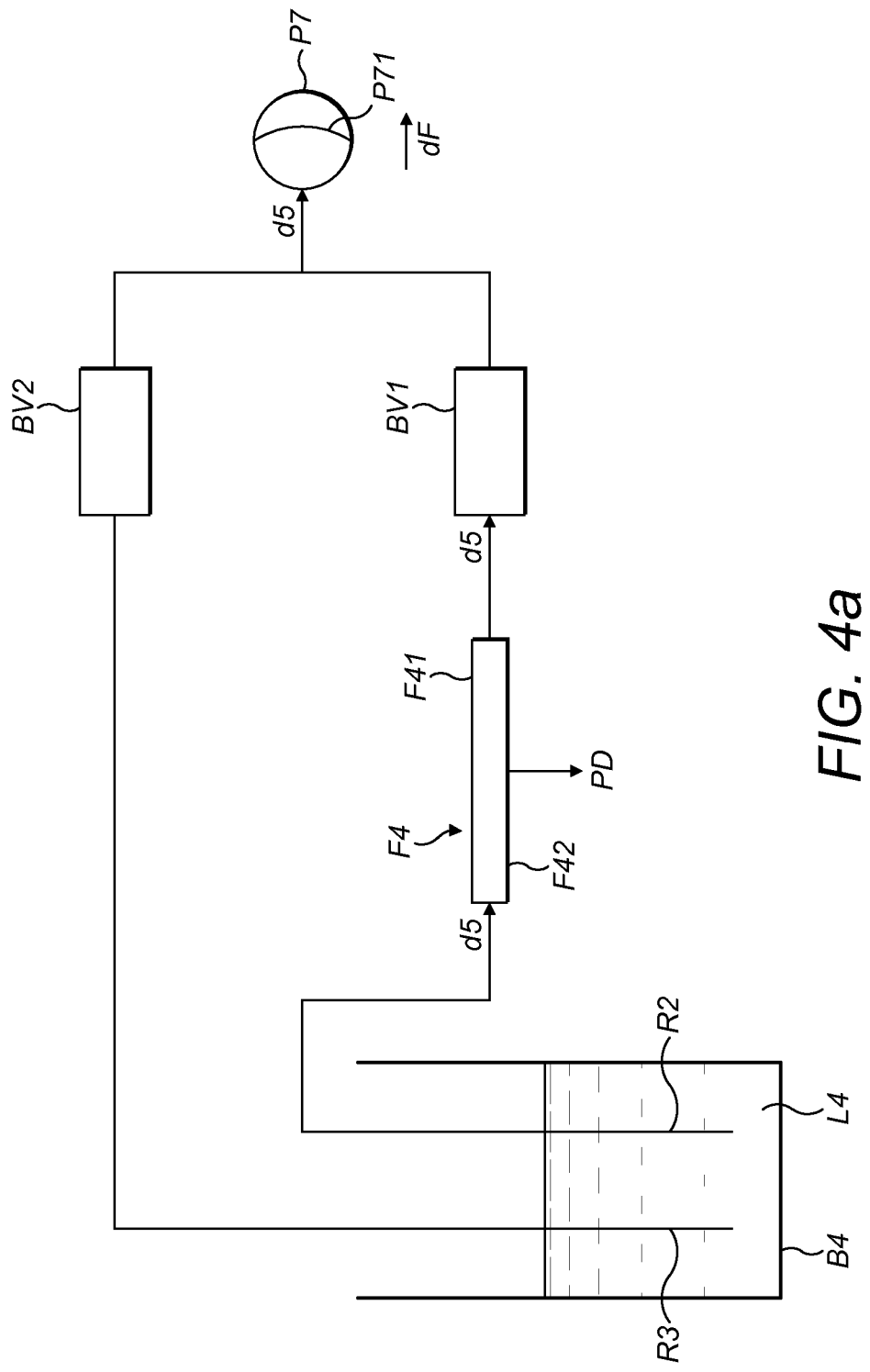
FIGS. 4a to 5b are simplified schematic representations of a liquid filtration system in accordance with a first embodiment of the invention, FIGS. 4a to 4d relating to TFF (tangential flow filtration) operation and FIGS. 5a and 5b relating to ATF (alternating tangential flow filtration) operation, thereof.

Referring in particular to FIG. 4a, in use the first bi-directional valve BV1 is controlled to be open and the second bi-directional valve BV2 is controlled to be closed. The perfusion pump P7 is operated such that the diaphragm P71 moves in a forward direction dF (rightwards in the sense of FIG. 4a) to cause displacement of the cell culture L4, in a first circuit flow direction d5, from the bioreactor vessel B4 to the perfusion pump P7 via the filter F4 and the first bi-directional valve BV1. Transfer of cell culture L4, from the bioreactor B4 into the filter F4, results in a positive driving pressure pD on the retentate side F41 of the membrane of the filter F4 which creates a trans-membrane pressure causing cell culture L4 to flow to the permeate side F42, thereby expelling the permeate material from the system.

Figure 4B:
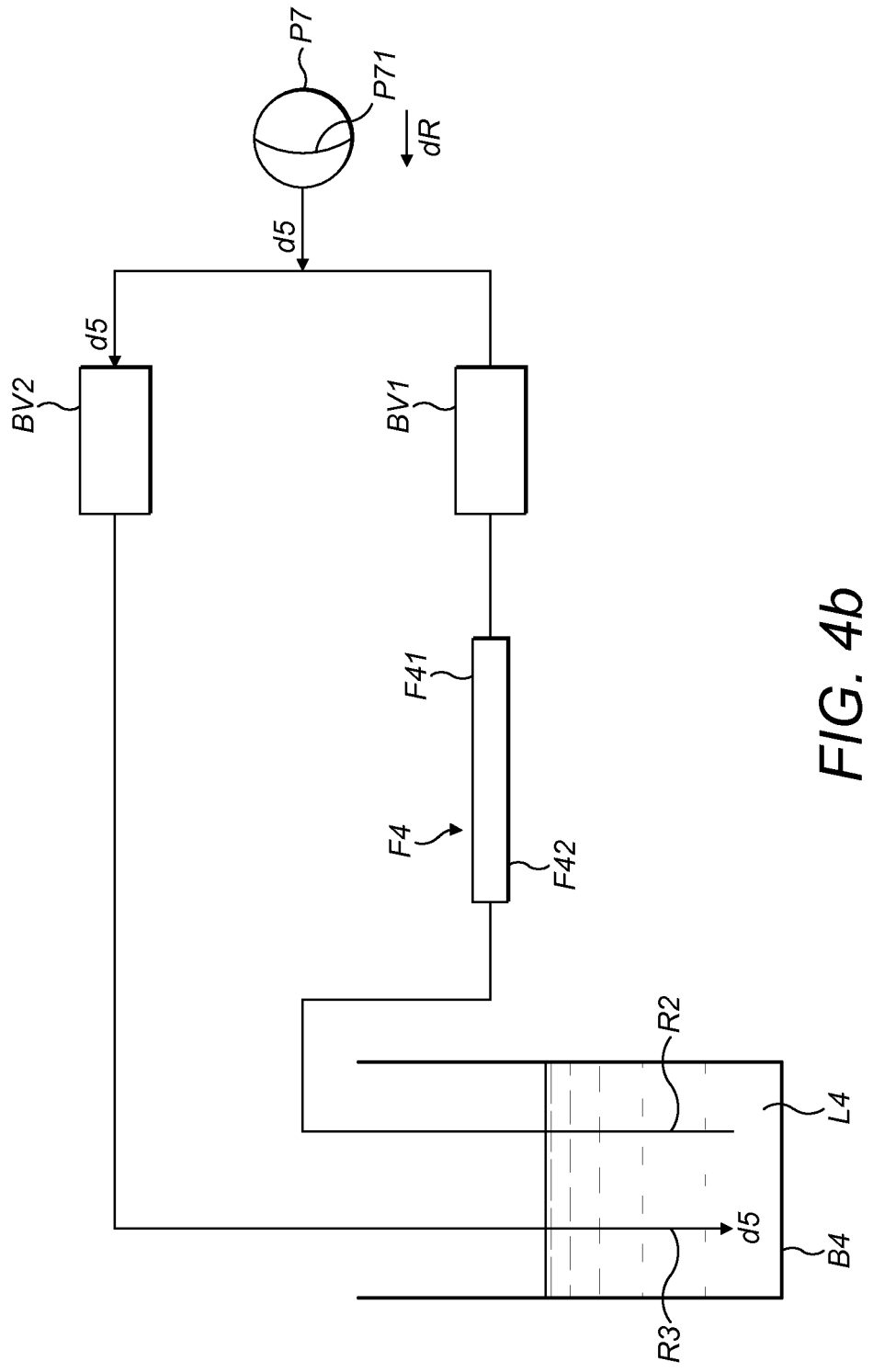

During (or alternatively immediately before or after) a brief pause, which occurs when the diaphragm P71 has reached the limit of travel in the forward direction dF, the first bi-directional valve BV1 is controlled to be closed and the second bi-directional valve BV2 is controlled to be open. Referring now to FIG. 4b, the diaphragm P71 moves in a rearward direction dR (leftwards in the sense of FIG. 4b) in order to displace the filtered cell culture L4, in the first circuit flow direction d5, back to the bioreactor vessel B4 via the second bi-directional valve BV2. Since the first bidirectional valve BV1 is closed, there is no back flow there through of the cell culture L4 to the filter F4.

The movements are repeated such that the diaphragm P71 continuously reciprocates in the forward and rearward directions dF, dR, and the first and second bi-directional valves BV1, BV2 are controlled to open and close as described above, in order to cycle the cell culture L4 through the filter F4. Thus the cell culture L4 is filtered and circulates in a "retentate loop" in a first circuit flow direction d5, i.e. anticlockwise in the sense of FIGS. 4a and 4b.

A second TFF operation of the first embodiment will now be described.

Figure 4C:
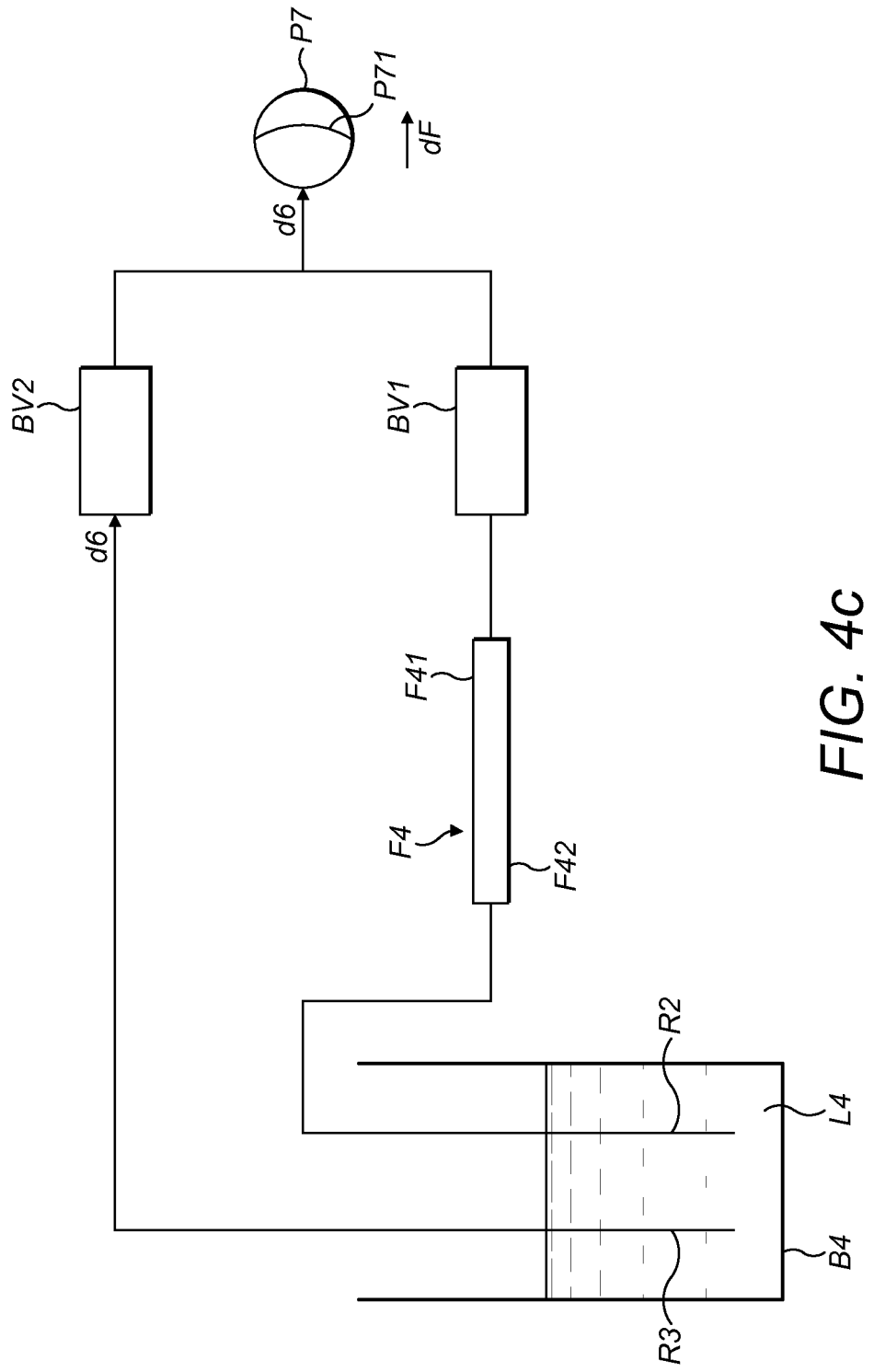

Referring in particular to FIG. 4c, in use the first bi-directional valve BV1 is controlled to be closed and the second bi-directional valve BV2 is controlled to be open. The perfusion pump P7 is operated such that the diaphragm P71 moves in the forward direction dF (rightwards in the sense of FIG. 4c) to cause displacement of the cell culture L4, in a second circuit flow direction d6, from the bioreactor vessel B4 to the perfusion pump P7 via the second bi-directional valve BV2.

Figure 4D:
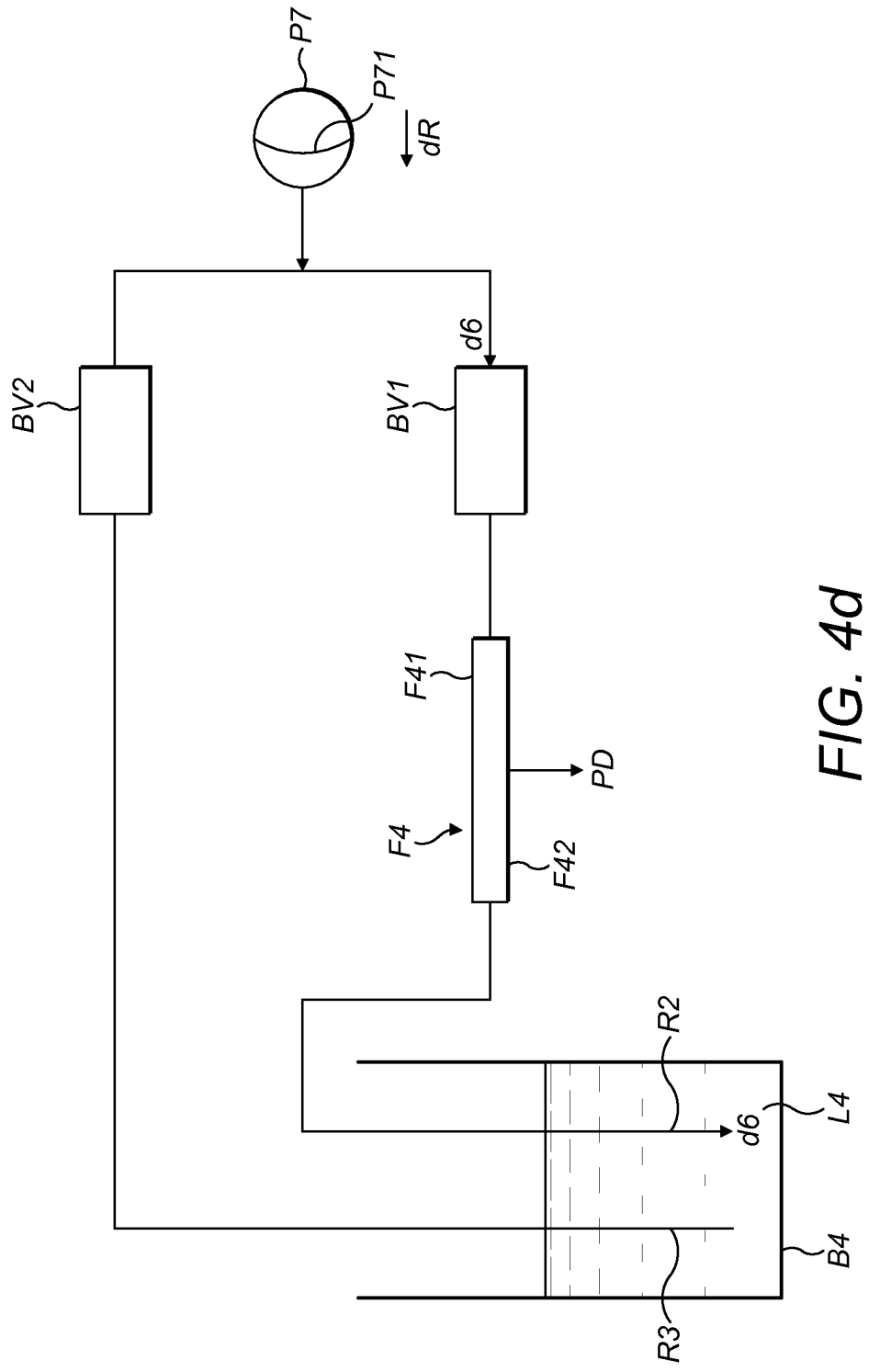

During (or alternatively immediately before or after) a brief pause, which occurs when the diaphragm P71 has reached the limit of travel in the forward direction dF, the first bi-directional valve BV1 is controlled to be open and the second bi-directional valve BV2 is controlled to be closed. Referring now to FIG. 4d, the diaphragm P71 moves in the rearward direction dR (leftwards in the sense of FIG. 4d) in order to displace the filtered cell culture L4, in the second circuit flow direction d6, back to the bioreactor vessel B4 via the first bi-directional valve BV1 and the filter F4. Since the second bi-directional valve BV2 is closed, there is no back flow there through of the cell culture L4 to the bioreactor vessel B4. The transfer of cell culture L4 back to the bioreactor vessel B4 via the filter F4 results in a positive driving pressure pD on the retentate side F41 of the membrane of the filter F4 which creates a trans-membrane pressure causing cell culture L4 to flow to the permeate side F42, thereby expelling the permeate material from the system.

The movements are repeated such that the diaphragm P71 continuously reciprocates in the forward and rearward directions dF, dR, and the first and second bi-directional valves BV1, BV2 are controlled to open and close as described above, in order to cycle the cell culture L4 through the filter F4. Thus the cell culture L4 is filtered and circulates in a "retentate loop" in a second circuit flow direction d6, i.e. clockwise in the sense of FIGS. 4c and 4d.

In view of the foregoing description and with reference to FIGS. 4a to 4d, in TFF operations the direction d5, d6 of the circuit flow, status of the first and second bi-directional valves BV1, BV2, and motion of the perfusion pump diaphragm P71, may be summarised as in the table below.

| Circuit flow direction | First bi-directional valve (BV1) | Second bi-directional valve (BV2) | Perfusion pump diaphragm (P71) | Reference FIG. |
|---|---|---|---|---|
| First (d5) | Open | Closed | Forward (dF) | 4a |
| | Closed | Open | Rearward (dR) | 4b |
| Second (d6) | Closed | Open | Forward (dF) | 4c |
| | Open | Closed | Rearward (dR) | 4d |

Thus the inventive system provides bi-directional valves BV1, BV2, which are controllable to open and close in co-ordination with the reciprocating perfusion pump P7, in order to enable two-way flow around the fluidic circuit of the system. In other words, the system operates in a TFF mode wherein the flow direction can be reversed because the opening and closing of the valves BV1, BV2 can be synchronised with the motion of the reciprocable element of the perfusion pump P7.

Also, the residence time of the cell culture in the system is reduced in comparison with the known system of FIGS. 3a and 3b, as follows. In that known system the diaphragm P51 of the perfusion pump P5 is moved, in the rearward direction dR, in order to return the filtered cell culture L3 to the bioreactor vessel B3, as has already been explained. Upon completion of that movement in the rearward direction dR, a portion of the filtered cell culture L3 will remain in the pipe/hose that defines the route R1 between the node N and the bioreactor vessel B3. Upon the next movement of the diaphragm P51 in the forward direction dF, which will pull cell culture L3 from the bioreactor vessel B3 through the filter F3, the said portion of the (already) filtered cell culture L3 will again pass through the filter F3 and be circulated around the system. As a result the cells in the said portion of cell culture L3 will spend an extended period of time in the "retentate loop", rather than being back in the bioreactor vessel B3 where the conditions are optimal for supporting cell growth. This period, known as "residence time", is known to be important with regard to healthy cell growth and is a key aspect of the design of cell perfusion systems. The described exemplary first embodiment of the invention deals with this problem, of extended residence time of a portion of the cell culture in a common bioreactor vessel inlet/outlet, by the provision of the above-mentioned separate and distinct inlet/outlet routes R2, R3 to/from the bioreactor vessel B4. That is, the invention provides an entirely separate route for the cell culture L4 back to the bioreactor vessel B4 following filtering. Thus in each filtering cycle the cell culture L4 is returned to the bioreactor vessel B4 where the conditions are optimal for supporting cell growth.

It will be understood by the skilled reader that the arrangement of the components of the system could differ from that of FIGS. 4a to 4d and yet the same reversible flow effect would still be achieved by the control of the bi-directional valves BV1, BV2. For example, the filter F4 could instead be located between the bioreactor vessel B4 and the second bi-directional valve BV2. Furthermore additional valves and/or filters may be included. All such alternative arrangements are within the scope of the claimed invention.

Figure 5A:
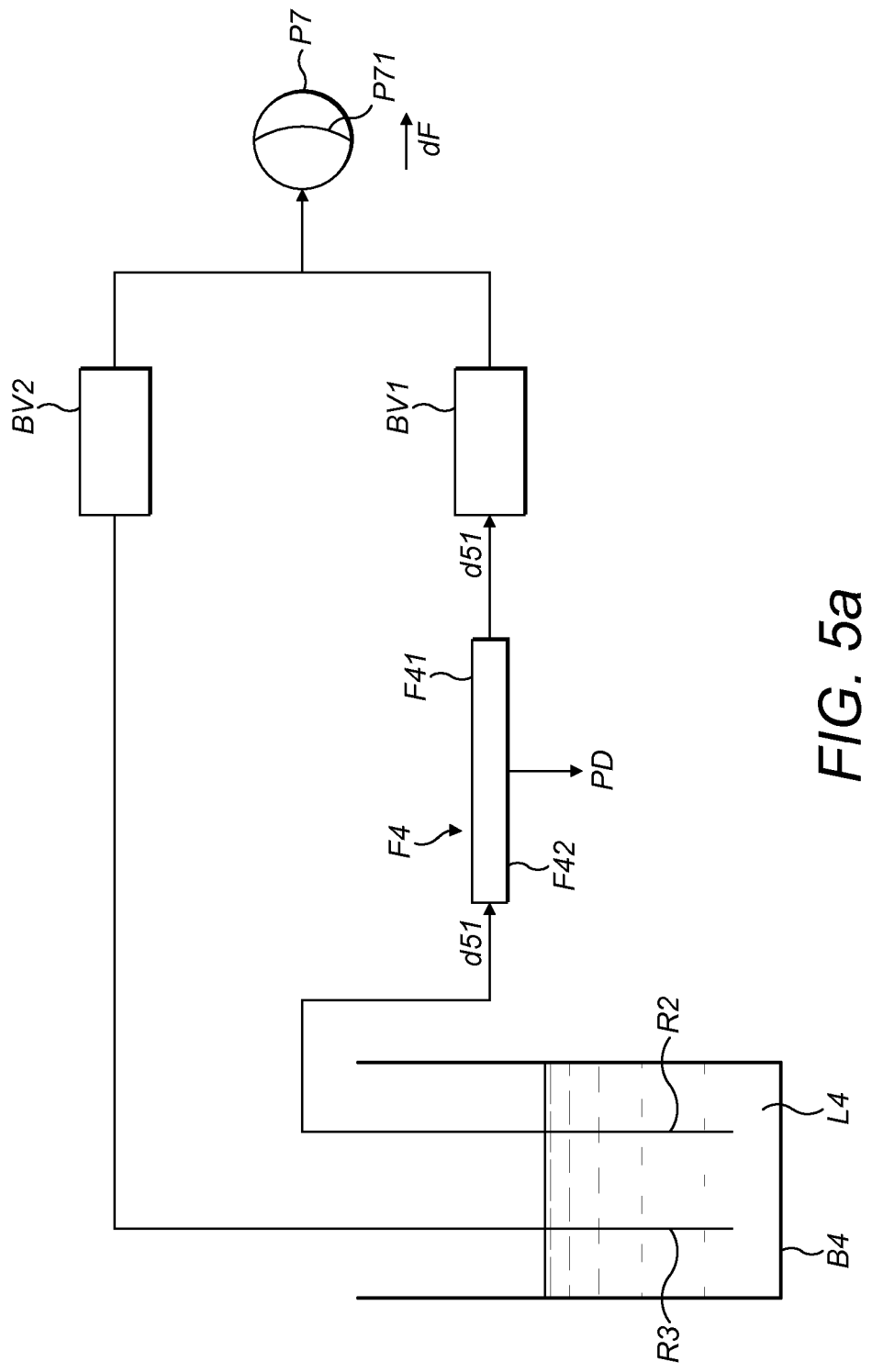
Figure 5B:
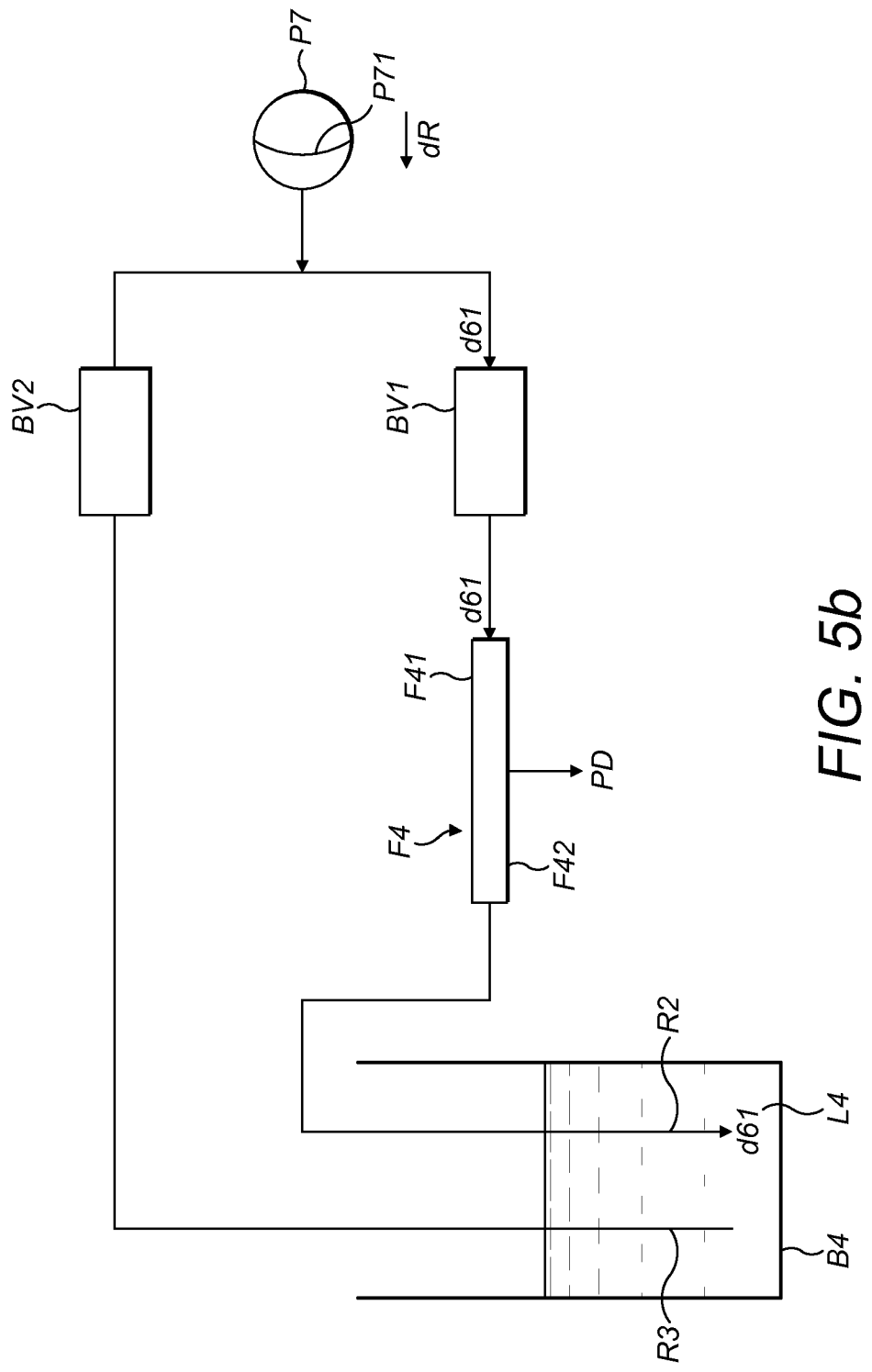

Turning to FIGS. 5a and 5b, an ATF (alternating tangential flow filtration) operation of the first embodiment will now be described.

Referring in particular to FIG. 5a, in use the first bi-directional valve BV1 is controlled to be open and the second bi-directional valve BV2 is controlled to be closed. The perfusion pump P7 is operated such that the diaphragm P71 moves in a forward direction dF (rightwards in the sense of FIG. 5a) to cause displacement of the cell culture L4, in a first alternating flow direction d51, from the bioreactor vessel B4 to the perfusion pump P7 via the filter F4 and the first bi-directional valve BV1.

During (or alternatively immediately before or after) a brief pause, which occurs when the diaphragm P71 has reached the limit of travel in the forward direction dF, the first bi-directional valve BV1 is controlled to remain open and the second bi-directional valve BV2 is controlled to remain closed. Referring now to FIG. 5b, the diaphragm P71 moves in a rearward direction dR (leftwards in the sense of FIG. 5b) in order to displace the filtered cell culture L4 in a second, opposite alternating flow direction d61, back to the bioreactor vessel B4 via the first bi-directional valve BV1. Since the second bi-directional valve BV2 remains closed, the return of the cell culture L4 to the bioreactor B4 is via the filter F4.

In each of the first and second alternating flow directions d51, d61, the transfer of cell culture L4 results in a positive driving pressure pD on the retentate side F41 of the membrane of the filter F4 which creates a trans-membrane pressure causing cell culture L4 to flow to the permeate side F42, thereby expelling the permeate material from the system.

The movements are repeated such that the diaphragm P71 continuously reciprocates in the forward and rearward directions dF, dR, all the while the first bi-directional valve BV1 remaining open and the second bidirectional valve BV2 remaining closed, in order to cycle the cell culture L4 back and forth through the filter F4.

In view of the foregoing description and still with reference to FIGS. 5a and 5b, the direction d51, d61 of the alternating flow, status of the first and second bi-directional valves BV1, BV2, and motion of the perfusion pump diaphragm P71, may be summarised as in the table below.

| Alternating flow direction | First bi-directional valve (BV1) | Second bi-directional valve (BV2) | Perfusion pump diaphragm (P71) | Reference FIG. |
|---|---|---|---|---|
| First (d51) | Open | Closed | Forward (dF) | 5a |
| Second (d61) | Open | Closed | Rearward (dR) | 5b |

Thus the cell culture L4 is filtered in an alternating flow through the filter F4. In other words, here the system performs in an ATF mode.

It will be understood by the skilled reader that the arrangement of the components of the system could differ from that of FIGS. 5a and 5b and yet the same alternating flow effect would still be achieved by the control of the bi-directional valves BV1, BV2. For example, the filter F4 could instead be located between the bioreactor vessel B4 and the second bi-directional valve BV2. In that case, for alternating flow the first bi-directional valve BV1 would be controlled to be closed while the second bi-directional valve BV2 would be controlled to be open. All such alternative arrangements are within the scope of the claimed invention.

From the foregoing it will be seen that the inventive system is a flexible, single system which has the capability to operate in a number of modes, as follows:
1. TFF-based perfusion
2. TFF-based perfusion with alteration of the flow direction at a prescribed period
3. ATF-based perfusion.

Figure 6:
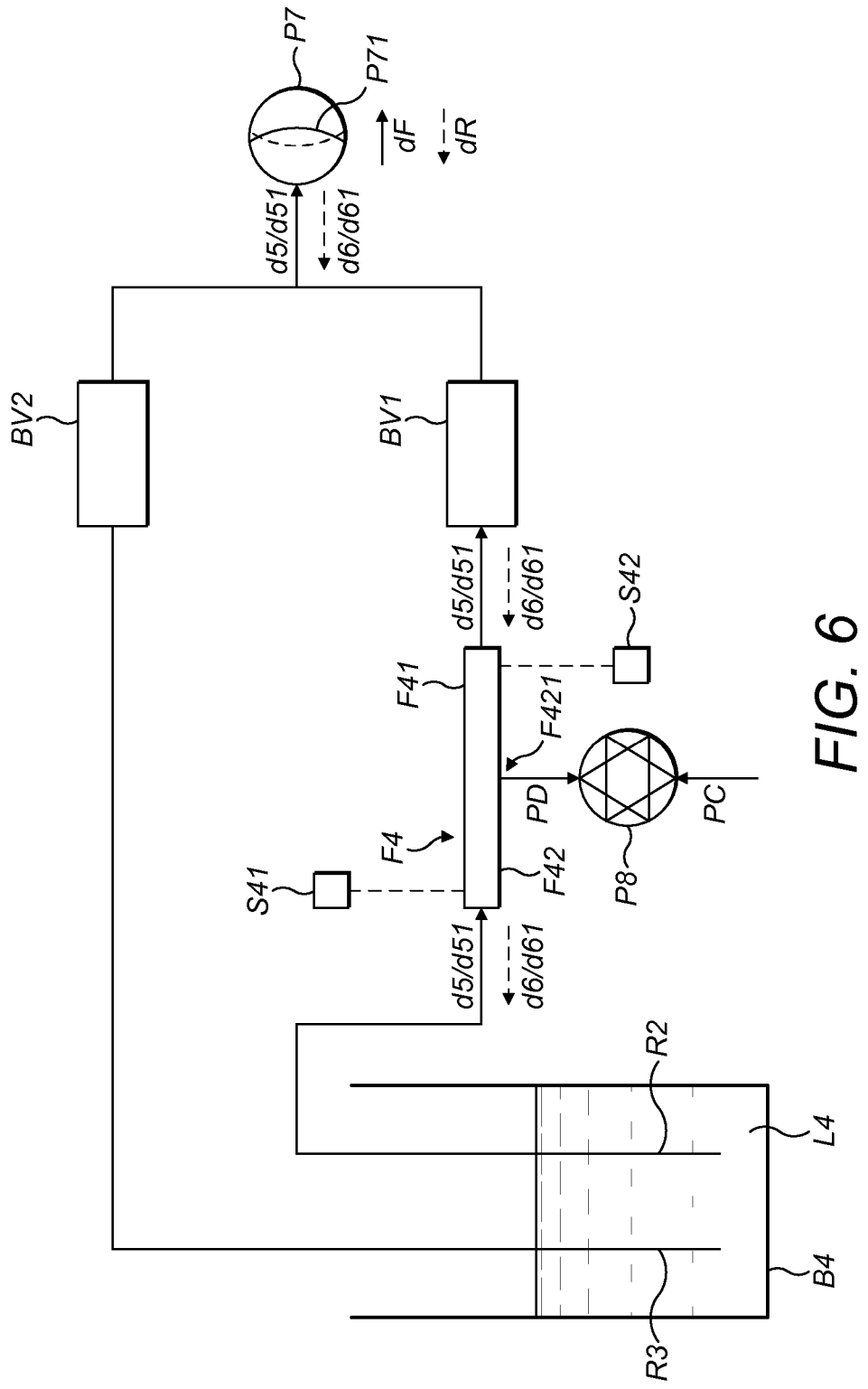
FIG. 6 is a simplified schematic representation of a liquid filtration system in accordance with a second embodiment of the invention and operations thereof.

Referring now to FIG. 6, there is provided a liquid filtration system for cell culture perfusion in accordance with a second embodiment of the invention. The second embodiment has in common with the first embodiment the bioreactor vessel B4 containing the liquid cell culture L4, the filter F4, the first and second bi-directional valves BV1, BV2, the perfusion pump P7 including the diaphragm P71, and the fluid connection means, and accordingly the same reference signs are used in the Figures.

The second embodiment also additionally includes a permeate pump P8 which is fluidly connected to a permeate side outlet F421 of the filter F4, and two pressure sensors S41, S42 which are configured to detect the fluidic pressure at the respective retentate and permeate sides F41, F42 of the filter membrane.

The operation of the second embodiment will now be described. It should be understood that, notwithstanding the addition of the permeate pump P8, the operation is broadly the same as that of the first embodiment, which has already been described above and, for the sake of brevity, will not be repeated in full here.

In use, transfer of the cell culture L4 from the bioreactor vessel B4 causes a positive driving pressure pD to be applied to the retentate side F41 of the membrane of the filter F4, as the cell culture L4 is displaced in the first circuit flow direction d5 due to movement of the diaphragm P71 in the forward direction dF (rightwards in the sense of FIG. 6). This driving pressure pD produces a trans-membrane pressure which tends to cause permeate material to pass through the membrane of the filter F4 from the retentate side F41 to the permeate side F42, thereby expelling the permeate material from the system, as has been described above. During the movement of the diaphragm P71 in the forward direction dF, the permeate pump is operated (in the same direction as the driving pressure pD) so as to contribute to the trans-membrane pressure, thereby increasing the rate of expulsion of the permeate material.

During the pause, which occurs when the diaphragm P71 has reached the limit of travel in the forward direction dF, a residual trans-membrane pressure may exist even though there is no longer a flow of liquid along the retentate side F41 at this point. As a result the filter F4 may become blocked with permeate material. The permeate pump P8 may therefore be controlled during the pause, and/or during a subsequent movement of the diaphragm P71 in the rearward direction dR (leftwards in the sense of FIG. 6), either to stop so as to no longer contribute to the trans-membrane pressure, or more preferably to apply a counter pressure pC to the permeate side F42 of the filter F4, which is in opposition to the residue of the driving pressure pD on the retentate side F41.

The counter pressure pC may be made equal to the residue of the driving pressure pD so that there will be no flow across the filter membrane. Alternatively, the counter pressure pC may be made greater than the residue of the driving pressure pD so that there will be a reverse flow across the filter membrane from the permeate side F42 to the retentate side F41. In each case, the effect of the counter pressure pC is to prevent (further) permeate material from passing through the membrane of the filter F4 from the retentate side F41 to the permeate side F42.

In this way a blockage of the filter F4 may be avoided, especially in the absence of a lateral flow on the retentate side F41 of the filter F4. In the case that the counter pressure pC exceeds the residual driving pressure pD to provide the said reverse flow, there is a cleaning effect on the filter F4 through the partial or complete displacement of solid permeate matter which has accumulated on the retentate side F41. The required magnitude of the applied counter pressure pC is determined according to the fluidic pressures which are detected by the pressure sensors (S41, S42) at the respective retentate and permeate sides F41, F42 of the filter F4.

In view of the foregoing description of the second embodiment and with reference still to FIG. 6, in TFF operations the direction d5, d6 of the circuit flow, status of the first and second bi-directional valves BV1, BV2, motion of the perfusion pump diaphragm P71, and motion of the permeate pump, may be summarised as in the table below.

| Circuit flow direction | First bi-directional valve (BV1) | Second bi-directional valve (BV2) | Perfusion pump diaphragm (P71) | Permeate pump (P8) |
|---|---|---|---|---|
| First (d5) | Open | Closed | Forward (dF) | Pump in direction pD |
| | Open | Closed | Paused at end of travel | Inactive or pump in direction pC |
| | Closed | Open | Rearward (dR) | Inactive or pump in direction pC |
| | Closed | Open | Paused at end of travel | Inactive or pump in direction pC |
| Second (d6) | Closed | Open | Forward (dF) | Inactive or pump in direction pC |
| | Closed | Open | Paused at end of travel | Inactive or pump in direction pC |
| | Open | Closed | Rearward (dR) | Pump in direction pD |
| | Open | Closed | Paused at end of travel | Inactive or pump in direction pC |

In ATF operations, the status of these system elements is as follows.

| Alternating flow direction | First bi-directional valve (BV1) | Second bi-directional valve (BV2) | Perfusion pump diaphragm (P71) | Permeate pump (P8) |
|---|---|---|---|---|
| First (d51) | Open | Closed | Forward (dF) | Pump in direction pD |
| | Open | Closed | Paused at end of travel | Inactive or pump in direction pC |
| Second (d61) | Open | Closed | Rearward (dR) | Pump in direction pD |
| | Open | Closed | Paused at end of travel | Inactive or pump in direction pC |

Hence it will be understood that the system of the second embodiment may be operated in a TFF mode (where the flow may be in a first circuit direction d5 or in a second, opposite circuit direction d6), and in an ATF mode (where the flow alternates between two opposite directions d51, d61), as has already been described in connection with the system of the first embodiment.

Thus the second embodiment of the inventive system provides a permeate pump P8 which is controllable to apply a counter pressure pC to the filter F4, in co-ordination with the reciprocating perfusion pump P7 (and the bi-directional valves BV1, BV2), in order to prevent permeate material from blocking the filter F4, or to clear a blockage which has occurred, in particular during a period where there is no lateral flow across the retentate F41 side of the filter F4. In other words, the filter F4 can be kept clear because the actuation of the permeate pump P8 can be synchronised with the motion of the reciprocable element of the perfusion pump P7. The fine control of neutral or back-pressure by the permeate pump P8 may be configured variably by the user and may utilise the pressure readings of the pressure sensors S41, S42 at the retentate and permeate sides F41, F42 of the filter F4.

It should be understood that the invention has been described in relation to its preferred embodiments and may be modified in many different ways without departing from the scope of the invention as defined by the accompanying claims.

The invention claimed is:
1. A reversible liquid filtration system for cell culture perfusion, comprising:
   a bioreactor vessel, for storing the cell culture;
   a perfusion pump, comprising a reciprocable element which is movable in opposing first and second pumping directions (dF, dR);
   a filter, comprising a membrane which includes a retentate side and an opposing, permeate side; and
   first and second bi-directional valves, each selectively controllable between open and closed positions,
   the perfusion pump, the filter, and the first and second bi-directional valves, together comprising a fluidic circuit in communication with the bioreactor vessel,
   wherein the filter is fluidly connected to the bioreactor vessel, the first bi-directional valve is fluidly connected to and positioned between the filter and the perfusion pump, and the second bi-directional valve is fluidly connected to and positioned between the perfusion pump and the bioreactor vessel, and
   the system being operable in a circuit flow mode, wherein:
   the first bi-directional valve is controllable to be open and the second bi-directional valve is controllable to be closed, and the reciprocable element of the perfusion pump is movable in the first pumping direction (dF), in order to displace the cell culture from the bioreactor vessel to the perfusion pump; and the first bi-directional valve is controllable to be closed and the second bi-directional valve is controllable to be open, and the reciprocable element of the perfusion pump is movable in the second pumping direction (dR), in order to displace the cell culture from the perfusion pump back to the bioreactor vessel, so as to displace the cell culture along the retentate side of the filter in a first circuit flow direction around the fluidic circuit, and
   the first bi-directional valve is controllable to be closed and the second bi-directional valve is controllable to be open, and the reciprocable element of the perfusion pump is movable in the first pumping direction (dF), in order to displace the cell culture from the bioreactor vessel to the perfusion pump; and the first bi-directional valve is controllable to be open and the second bi-directional valve is controllable to be closed, and the reciprocable element of the perfusion pump is movable in the second pumping direction (dR), in order to displace the cell culture from the perfusion pump back to the bioreactor vessel, so as to displace the cell culture along the retentate side of the filter in a second circuit flow direction around the fluidic circuit, the second circuit flow direction being opposite to the first circuit flow direction,
   and the system being operable in an alternating flow mode, wherein:
   the first bi-directional valve is controllable to be open and the second bi-directional valve is controllable to be closed;
   the reciprocable element of the perfusion pump is movable in the first pumping direction (dF), in order to displace the cell culture from the bioreactor vessel along the retentate side of the filter to the perfusion pump in a first alternating flow direction; and
   the reciprocable element of the perfusion pump is movable in the second pumping direction (dR), in order to displace the cell culture from the perfusion pump along the retentate side of the filter back to the bioreactor vessel in a second alternating flow direction, the second alternating flow direction being opposite to the first alternating flow direction, in each of the circuit flow mode and the alternating flow mode the said displacement of the cell culture along the retentate side of the filter causing a driving fluid pressure (pD) on the retentate side of the filter membrane such that permeate material may pass through the membrane from the retentate side to the permeate side.

2. A reversible liquid filtration system according to claim 1, comprising a controller for controlling the first and second bi-directional valves in co-ordination with the movement of the reciprocable element of the perfusion pump.

3. A reversible liquid filtration system according to claim 1, further comprising:
pressure sensors, configured to detect fluidic pressure at the respective retentate and permeate sides of the filter membrane; and
a permeate pump, arranged in fluidic communication with the filter and controllable to apply, based on the detected fluidic pressures, a counter fluid pressure (pC) on the permeate side of the filter membrane, in opposition to a residue of the said driving fluid pressure (pD) on the retentate side, such that no permeate material may pass through the membrane from the retentate side to the permeate side.

4. A reversible liquid filtration system according to claim 3, wherein the permeate pump is controllable to apply the counter fluid pressure (pC), to the permeate side of the filter membrane, at a magnitude which is:
equal to the residue of the driving fluid pressure (pD) on the retentate side, so as to prevent permeate material from passing through the membrane from the retentate side to the permeate side; or
greater than the residue of the driving fluid pressure (pD) on the retentate side, so as to reverse the flow through the membrane to partially or fully clear the retentate side of the membrane of permeate material.

5. A reversible liquid filtration system according to claim 3, wherein the permeate pump is controllable to control a pressure gradient, between the retentate and permeate sides of the filter membrane, in order to control the passage of permeate material through the membrane, from the retentate side to the permeate side, under the residue of the driving fluid pressure (pD) on the retentate side.

6. A reversible liquid filtration system according to claim 3, comprising a controller for controlling in co-ordination the first and second bi-directional valves, the movement of the reciprocable element of the perfusion pump, and the permeate pump.

7. A reversible liquid filtration system according to claim 1, wherein the reciprocable element of the perfusion pump comprises a piston.

8. A reversible liquid filtration system according to claim 1, wherein the reciprocable element of the perfusion pump comprises a diaphragm.

9. A reversible liquid filtration system according to claim 1, wherein the bioreactor vessel comprises at least two separate liquid inlets/outlets.

10. A reversible liquid filtration system for cell culture perfusion, comprising:
a bioreactor vessel, for storing the cell culture;
a perfusion pump, comprising a reciprocable element which is movable in opposing first and second pumping directions (dF, dR);
a filter, comprising a membrane which includes a retentate side and an opposing, permeate side; and
first and second bi-directional valves, each selectively controllable between open and closed positions,
the perfusion pump, the filter, and the first and second bi-directional valves, together comprising a fluidic circuit in communication with the bioreactor vessel,
wherein the filter is fluidly connected to the bioreactor vessel, the first bi-directional valve is fluidly connected to and positioned between the filter and the perfusion pump, and the second bi-directional valve is fluidly connected to and positioned between the perfusion pump and the bioreactor vessel, and
wherein, in dependence on the selected positions of the first and second bi-directional valves and the pumping direction (dF, dR), the system is selectively operable between:
a reversible circuit flow mode, wherein the cell culture will flow, around the fluidic circuit, in a first circuit flow direction or in a second circuit flow direction which is opposite to the first circuit flow direction; and
an alternating flow mode, wherein the cell culture will alternately flow, around only a portion of the fluidic circuit, between a first alternating flow direction and in a second alternating flow direction which is opposite to the first alternating flow direction,
and wherein, in each of the circuit flow mode and the alternating flow mode, the perfusion pump is operable to displace the cell culture along the retentate side of the filter to cause a driving fluid pressure (pD) on the retentate side of the filter membrane such that permeate material may pass through the membrane from the retentate side to the permeate side.

11. A reversible liquid filtration system according to claim 10, wherein in the reversible circuit flow mode:
the first bi-directional valve is controllable to be open and the second bi-directional valve is controllable to be closed, and the reciprocable element of the perfusion pump is movable in the first pumping direction (dF), in order to displace the cell culture from the bioreactor vessel to the perfusion pump; and the first bi-directional valve is controllable to be closed and the second bi-directional valve is controllable to be open, and the reciprocable element of the perfusion pump is movable in the second pumping direction (dR), in order to displace the cell culture from the perfusion pump back to the bioreactor vessel, so as to displace the cell culture along the retentate side of the filter in the first circuit flow direction around the fluidic circuit, and
the first bi-directional valve is controllable to be closed and the second bi-directional valve is controllable to be open, and the reciprocable element of the perfusion pump is movable in the first pumping direction (dF), in order to displace the cell culture from the bioreactor vessel to the perfusion pump; and the first bi-directional valve is controllable to be open and the second bi-directional valve is controllable to be closed, and the reciprocable element of the perfusion pump is movable in the second pumping direction (dR), in order to displace the cell culture from the perfusion pump back to the bioreactor vessel, so as to displace the cell culture along the retentate side of the filter in the second circuit flow direction around the fluidic circuit,
and wherein in the alternating flow mode:
the first bi-directional valve is controllable to be open and the second bi-directional valve is controllable to be closed;
the reciprocable element of the perfusion pump is movable in the first pumping direction (dF), in order to displace the cell culture from the bioreactor vessel along the retentate side of the filter to the perfusion pump in the first alternating flow direction; and the reciprocable element of the perfusion pump is movable in the second pumping direction (dR), in order to displace the cell culture from the perfusion pump along the retentate side of the filter back to the bioreactor vessel in the second alternating flow direction.

12. A reversible liquid filtration system according to claim 10, comprising a controller for controlling the first and second bi-directional valves in co-ordination with the movement of the reciprocable element of the perfusion pump.

13. A reversible liquid filtration system according to claim 10, comprising:

pressure sensors, configured to detect fluidic pressure at the respective retentate and permeate sides of the filter membrane; and a permeate pump, arranged in fluidic communication with the filter and controllable to apply, based on the detected fluidic pressures, a counter fluid pressure (pC) on the permeate side of the filter membrane, in opposition to a residue of the said driving fluid pressure (pD) on the retentate side, such that no permeate material may pass through the membrane from the retentate side to the permeate side.

14. A reversible liquid filtration system according to claim 13, wherein the permeate pump is controllable to apply the counter fluid pressure (pC), to the permeate side of the filter membrane, at a magnitude which is:

equal to the residue of the driving fluid pressure (pD) on the retentate side, so as to prevent permeate material from passing through the membrane from the retentate side to the permeate side; or greater than the residue of the driving fluid pressure (pD) on the retentate side, so as to reverse the flow through the membrane to partially or fully clear the retentate side of the membrane of permeate material.

15. A reversible liquid filtration system according to claim 13, wherein the permeate pump is controllable to control a pressure gradient, between the retentate and permeate sides of the filter membrane, in order to control the passage of permeate material through the membrane, from the retentate side to the permeate side, under the residue of the driving fluid pressure (pD) on the retentate side.

16. A reversible liquid filtration system according to claim 13, comprising a controller for controlling in co-ordination the first and second bi-directional valves, the movement of the reciprocable element of the perfusion pump, and the permeate pump.

17. A reversible liquid filtration system according to claim 10, wherein the reciprocable element of the perfusion pump comprises a piston.

18. A reversible liquid filtration system according to claim 10, wherein the reciprocable element of the perfusion pump comprises a diaphragm.

19. A reversible liquid filtration system according to claim 10, wherein the bioreactor vessel comprises at least two separate liquid inlets/outlets.

* * * * *